(12) United States Patent
Ahn et al.

(10) Patent No.: US 10,640,650 B2
(45) Date of Patent: May 5, 2020

(54) PHTHALONITRILE COMPOUND

(71) Applicant: LG CHEM, LTD., Seoul (KR)

(72) Inventors: Ki Ho Ahn, Daejeon (KR); Sang Woo Kim, Daejeon (KR); Seung Hee Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/779,230

(22) PCT Filed: Dec. 2, 2016

(86) PCT No.: PCT/KR2016/014090
§ 371 (c)(1),
(2) Date: May 25, 2018

(87) PCT Pub. No.: WO2017/095177
PCT Pub. Date: Jun. 8, 2017

(65) Prior Publication Data
US 2018/0355180 A1    Dec. 13, 2018

(30) Foreign Application Priority Data
Dec. 2, 2015 (KR) .................. 10-2015-0170873

(51) Int. Cl.
| C09B 47/067 | (2006.01) |
|---|---|
| C08L 79/00 | (2006.01) |
| C07C 255/54 | (2006.01) |
| C09B 47/06 | (2006.01) |
| C08L 33/18 | (2006.01) |
| C07C 255/51 | (2006.01) |

(52) U.S. Cl.
CPC .......... *C09B 47/067* (2013.01); *C07C 255/54* (2013.01); *C08L 79/00* (2013.01); *C09B 47/063* (2013.01); *C07C 255/51* (2013.01); *C08L 33/18* (2013.01)

(58) Field of Classification Search
CPC ... C09B 47/067; C09B 47/063; C07C 255/54; C07C 255/51; C08L 79/00; C08L 33/18
USPC ..................................................... 540/143
See application file for complete search history.

(56) References Cited

FOREIGN PATENT DOCUMENTS

| CN | 102936340 A | 2/2013 |
|---|---|---|
| CN | 102976972 A | 3/2013 |
| CN | 102993070 A | 3/2013 |
| CN | 103881309 A | 6/2014 |
| KR | 10-2001-0072625 A | 7/2001 |
| KR | 10-0558158 A | 2/2006 |
| KR | 10-2016-0137131 A | 11/2016 |
| WO | 01/18301 A1 | 3/2001 |

OTHER PUBLICATIONS

Ozer. L. M. et al., "Synthesis, Characterization, OFET and Electrochemical Properties of Novel Dimeric Metallophthalocyanines", Dalton Trans., 2013 [Electronic publishing: Feb. 19, 2013], vol. 42, pp. 6633-6644.

*Primary Examiner* — Kristin A Vajda
(74) *Attorney, Agent, or Firm* — Dentons US LLP

(57) ABSTRACT

The present application can provide a phthalonitrile compound and a use thereof. The phthalonitrile compound has a novel structure, and can exhibit an excellent effect in a use to which the phthalonitrile compound can be applied. An example of the use of the phthalonitrile compound may be a raw material or precursor for, so-called, a phthalonitrile resin, a phthalocyanine dye, a fluorescent whitening agent, a photographic sensitizer, an acid anhydride, or the like.

11 Claims, 2 Drawing Sheets

PHTHALONITRILE COMPOUND

CROSS-REFERENCE TO RELATED APPLICATIONS

This application is a National Stage Entry of International Application No. PCT/KR2016/014090 filed on Dec. 2, 2016, and claims the benefit of Korean Application No. 10-2015-0170873 filed on Dec. 2, 2015, all of which are hereby incorporated by reference in their entirety for all purposes as if fully set forth herein.

TECHNICAL FIELD

The present application relates to a phthalonitrile compound, a phthalonitrile resin, a polymerizable composition, a prepolymer, a composite, a precursor thereof, and a production method and use thereof.

BACKGROUND ART

The phthalonitrile compound can be applied to various applications. For example, a phthalonitrile compound can be used as a raw material of a so-called phthalonitrile resin. For example, a composite formed by impregnating a phthalonitrile resin into a filler such as glass fiber or carbon fiber can be used as a material for automobiles, airplanes or ships. The process for producing the composite may include, for example, a process of mixing a mixture of phthalonitrile and a curing agent or a prepolymer formed by the reaction of the mixture with a filler and then curing the mixture (see, for example, Patent Document 1).

The other use of phthalonitrile compounds may include a use as precursors of phthalocyanine dyes. For example, a phthalonitrile compound may be compounded with a metal to be applied as a pigment.

The phthalonitrile compound can also be applied as a precursor of a fluorescent brightener or a photographic sensitizer or a precursor of an acid anhydride, and the like. For example, the phthalonitrile compound can be converted to an acid anhydride via an appropriate oxidation process and dehydration process, and such an acid anhydride can also be used as a precursor of polyamic acid or polyimide, and the like.

(Patent Document 1) Korean Patent No. 0558158

DISCLOSURE

Technical Problem

The present application can provide a novel phthalonitrile compound and a use thereof. As the use, a phthalonitrile resin, a polymerizable composition or a prepolymer for preparing the same, a composite, a precursor for the composite, or the like, or a precursor or a raw material for a pigment, a fluorescent brightener, a photo sensitizer or an acid anhydride can be exemplified.

Technical Solution

The present application relates to a phthalonitrile compound. The compound may be represented by Formula 1 below.

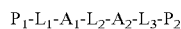   [Formula 1]

In Formula 1, $P_1$ and $P_2$ are the same or different aryl groups from each other, $A_1$ and $A_2$ are the same or different arylene groups from each other, $L_1$ to $L_3$ are each independently an alkylene group, an alkylidene group, an alkenylene group or an alkynylene group, and $P_1$, $P_2$, $A_1$ and $A_2$ are each substituted with at least one substituent represented by Formula 2 below.

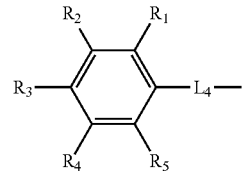   [Formula 2]

In Formula 2, $L_4$ is an alkylene group, an alkylidene group, an oxygen atom or a sulfur atom, and $R_1$ to $R_5$ are each independently hydrogen, an alkyl group, an alkoxy group, an aryl group or a cyano group, provided that at least two of $R_1$ to $R_5$ are a cyano group.

In the present application, the term alkyl group may be an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be linear, branched or cyclic and, if necessary, may be substituted with one or more substituents.

In the present application, the term alkoxy group may be an alkoxy group having 1 to 20 carbon atoms, 1 to 16 carbon atoms, 1 to 12 carbon atoms, 1 to 8 carbon atoms or 1 to 4 carbon atoms, unless otherwise specified. The alkoxy group may be linear, branched or cyclic, and, if necessary, may be substituted with one or more substituents.

In the present application, the term alkylene group or alkylidene group may mean an alkylene group or alkylidene group having 1 to 20 carbon atoms, 1 to 16 carbon atoms, 1 to 12 carbon atoms, 1 to 8 carbon atoms, or 1 to 4 carbon atoms, unless otherwise specified. The alkylene group or alkylidene group may be linear, branched or cyclic. In addition, the alkylene group or alkylidene group may be optionally substituted with one or more substituents.

In the present application, the term alkenylene group or alkynylene group may mean an alkenylene group or alkynylene group having 2 to 20 carbon atoms, 2 to 16 carbon atoms, 2 to 12 carbon atoms, 2 to 8 carbon atoms, or 2 to 4 carbon atoms, unless otherwise specified. The alkenylene group or alkynylene group may be linear, branched or cyclic. In addition, the alkenylene group or alkynylene group may be optionally substituted with one or more substituents.

In the present application, the term aryl group is a monovalent residue derived from an aromatic compound and the arylene group is a divalent residue derived from an aromatic compound, unless otherwise specified. Here, the monovalent residue may mean a case where a radical generated by leaving one hydrogen atom of the aromatic compound forms a covalent bond, such as, for example, a phenyl group, and the divalent residue may means a case where a radical generated by leaving two hydrogen atoms of the aromatic compound forms two covalent bonds, such as, for example, phenylene.

In the above, the aromatic compound may mean benzene, a benzene structure containing compound or any one derivative thereof. Here, the benzene containing compound may mean a compound having a structure in which two or more benzene rings are condensed while sharing one or two carbon atoms or are linked directly or by an appropriate linker. Such a compound can be exemplified by biphenyl or naphthalene, and the like.

The aryl group or arylene group may comprise, for example, 6 to 25, 6 to 20, 6 to 15, or 6 to 12 carbon atoms. A specific kind of the aryl group can be exemplified by a phenyl group, a benzyl group, a biphenyl group or a naphthalenyl group, and the like, and an example of the arylene group can be exemplified by a phenylene group, and the like, without being limited thereto.

As the substituent with which the alkyl group, alkoxy group, aryl group, aromatic divalent radical, alkylene group or alkylidene group can be optionally substituted, halogen, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkoxy group or an aryl group, and the like can be exemplified, without being limited thereto.

In the compound of Formula 1, $L_1$ to $L_3$ may be each independently an alkylene group or alkylidene group having 1 to 4 carbon atoms, and may be, for example, a methylene group or an ethylene group. When $L_1$ to $L_3$ are each independently a methylene group or an ethylene group, the compound of Formula 1 can provide a prepolymer having excellent processability and a phthalonitrile resin having excellent heat resistance.

In the compound of Formula 1, $P_1$, $P_2$, $A_1$ and $A_2$ are an aryl group or an arylene group, as described above, where each of these can be substituted with at least one or more substituents of Formula 2 above.

In the above $P_1$, $P_2$, $A_1$ and $A_2$, other substituents may be present in addition to the substituent of Formula 2, where an example thereof include halogen, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkoxy group or an aryl group, and the like, in a suitable example, an alkyl group may be substituted, and preferably, a methyl group may be substituted. When the methyl group is substituted, the compound of Formula 1 can provide a prepolymer having excellent processability and a phthalonitrile resin having excellent heat resistance.

That is, each of $P_1$, $P_2$, $A_1$ and $A_2$ may be substituted with at least one substituent of Formula 2 above and alkyl group.

In Formula 1, $A_1$ and $A_2$ may be an arylene group having 6 to 25, 6 to 20, 6 to 15 or 6 to 12 carbon atoms, and may be, for example, a phenylene group.

When $A_1$ and $A_2$ are a phenylene group, the positions of $L_1$ to $L_3$ connected to both are not particularly limited. For example, in the case of $A_1$, $L_1$ may be bonded to an ortho, meta, or para position based on the position combined with $L_2$. Also, in the case of $A_2$, $L_3$ may also be bonded to an ortho, meta, or para position based on the position combined with $L_2$.

In one example, in the case of $A_1$, $L_1$ may be bonded to the meta position based on the position combined with $L_2$. Also, in the case of $A_2$, $L_3$ may be bonded to the meta position based on the position combined with $L_2$. Such a structure may be advantageous to maintain a suitable processing temperature and a wide process window in the process of preparing the phthalonitrile resin.

When $A_1$ and $A_2$ are a phenylene group, the position of the substituent of Formula 2 above with which each is substituted may be adjusted. For example, in the case of $A_1$, the substituent of Formula 2 may be substituted at an ortho, meta or para position based on the position combined with $L_2$. Also, in the case of $A_2$, the substituent of Formula 2 may also be substituted at an ortho, meta or para position based on the position combined with $L_2$.

In one example, in the case of $A_1$, the substituent of Formula 2 may be bonded to the para position based on the position combined with $L_2$. Also, in the case of $A_2$, the substituent of Formula 2 may be bonded to the para position based on the position combined with $L_2$. Such a structure may be advantageous to maintain a suitable processing temperature and a wide process window in the process of preparing the phthalonitrile resin.

Other substituents may be present in $A_1$ and $A_2$, which are a phenylene group, and the example thereof can be exemplified by an alkyl group, specifically, an alkyl group having 1 to 4 carbon atoms or a methyl group or an ethyl group. For example, in the case of $A_1$, the alkyl group may be substituted at an ortho, meta, or para position based on the position combined with $L_2$. Also, in the case of $A_2$, the alkyl group may also be substituted at an ortho, meta, or para position based on the position combined with $L_2$.

In one example, in the case of $A_1$, the alkyl group may be substituted at the meta position based on the position combined with $L_2$. Also, in the case of $A_2$, the alkyl group may be substituted at the meta position based on the position combined with $L_2$. Such a structure may be advantageous to maintain a suitable processing temperature and a wide process window in the process of preparing the phthalonitrile resin.

In one example, when $A_1$ is phenylene, where the number of the carbon atom bonded to $L_2$ is 1 and the carbon atoms are numbered in the clockwise direction, the compound may have a structure in which the alkyl group is substituted at the 3-carbon atom, the substituent of Formula 2 above is substituted at the 4-carbon atom and the 5-carbon atom is combined with the $L_1$.

In one example, when $A_2$ is phenylene, where the number of the carbon atom bonded to $L_2$ is 1 and the carbon atoms are numbered in the clockwise direction, the compound may have a structure in which the alkyl group is substituted at the 5-carbon atom, the substituent of Formula 2 above is substituted at the 4-carbon atom and the 3-carbon atom is combined with the $L_3$. Such a structure may be advantageous to maintain a suitable processing temperature and a wide process window in the process of preparing the phthalonitrile resin.

In Formula 1, $P_1$ and $P_2$ may be an aryl group having 6 to 25, 6 to 20, 6 to 15 or 6 to 12 carbon atoms, and may be, for example, a phenyl group.

When $P_1$ and $P_2$ are a phenyl group, the position of the substituent of Formula 2 above with which each is substituted may be adjusted. For example, in the case of $P_1$, the substituent of Formula 2 may be substituted at an ortho, meta or para position based on the position combined with $L_1$. Also, in the case of $P_2$, the substituent of Formula 2 may also be substituted at an ortho, meta or para position based on the position combined with $L_3$.

In one example, in the case of $P_1$, the substituent of Formula 2 may be bonded to the ortho position based on the position combined with $L_1$. Also, in the case of $P_2$, the substituent of Formula 2 may be bonded to the ortho position based on the position combined with $L_3$. Such a structure may be advantageous to maintain a suitable processing temperature and a wide process window in the process of preparing the phthalonitrile resin.

Other substituents may be present in $P_1$ and $P_2$, which are a phenylene group, and the example thereof can be exemplified by an alkyl group, specifically, an alkyl group having 1 to 4 carbon atoms or a methyl group or an ethyl group. For example, in the case of $P_1$, the alkyl group may be substituted at an ortho, meta, or para position based on the position combined with $L_1$. Also, in the case of $P_2$, the alkyl group may also be substituted at an ortho, meta, or para position based on the position combined with $L_3$.

In one example, in the case of $P_1$, the alkyl group may be substituted at the meta position based on the position combined with $L_1$. Also, in the case of $P_2$, the alkyl group may be substituted at the meta position based on the position combined with $L_3$. Such a structure may be advantageous to maintain a suitable processing temperature and a wide process window in the process of preparing the phthalonitrile resin.

In one example, when $P_1$ is a phenyl group, where the number of the carbon atom bonded to $L_1$ is 1 and the carbon atoms are numbered in the clockwise direction, the compound may have a structure in which the alkyl group is substituted at the 3-carbon atom and the substituent of Formula 2 above is substituted at the 6-carbon atom.

In one example, when $P_2$ is phenylene, where the number of the carbon atom bonded to $L_3$ is 1 and the carbon atoms are numbered in the clockwise direction, the compound may have a structure in which the alkyl group is substituted at the 5-carbon atom and the substituent of Formula 2 above is substituted at the 2-carbon atom.

Such a structure may be advantageous to maintain a suitable processing temperature and a wide process window in the process of preparing the phthalonitrile resin.

In Formula 2, $L_4$ is an alkylene group, an alkylidene group, an oxygen atom or a sulfur atom, and for example, may be an oxygen atom.

$R_1$ to $R_5$ are each independently hydrogen, an alkyl group, an alkoxy group, an aryl group or a cyano group, provided that at least two of $R_1$ to $R_5$ are a cyano group. For example, any two of $R_2$ to $R_4$ may be a cyano group, and in another example, it may also have a structure in which $R_3$ is a cyano group and $R_2$ or $R_4$ is a cyano group. Among $R_1$ to $R_5$, the substituent which is not a cyano group may be a hydrogen atom or an alkyl group.

The compound of Formula 1 can be synthesized according to a known synthesis method of an organic compound. For example, the compound of Formula 1 can be synthesized by a reaction known as a so-called nitro displacement reaction, for example, a method of reacting a hydroxy group containing compound and a nitrile group containing compound in the presence of a basic catalyst or the like.

The present application also relates to a use of the compound. As the use of the compound, a raw material or a precursor of a phthalonitrile resin, a phthalocyanine dye, a fluorescent brightener, a photographic sensitizer or an acid anhydride can be exemplified, as described above. As one example of the use, for example, the present application may be directed to a phthalonitrile resin. The phthalonitrile resin may contain a polymerized unit derived from the compound of the Formula 1. In the present application, the term polymerized unit derived from a certain compound may mean a skeleton of a polymer formed by polymerization or curing of the compound.

Also, the phthalonitrile resin may further comprise a polymerized unit of other phthalonitrile compounds in addition to the polymerized unit of the compound of Formula 1. In this case, the kind of the phthalonitrile compound capable of being selected and used is not particularly limited and the known compounds known to be useful for forming the phthalonitrile resin and controlling its physical properties can be applied. As an example of such a compound, compounds disclosed in U.S. Pat. No. 4,408,035, 5,003,039, 5,003,078, 5,004,801, 5,132,396, 5,139,054, 5,208,318, 5,237,045, 5,292,854, or 5,350,828 can be exemplified, but is not limited thereto.

In the phthalonitrile resin, the polymerization unit of the compound of Formula 1 may be a polymerized unit formed by the reaction of the above compound with a curing agent. The kind of the curing agent that can be used in this case is not particularly limited as long as it is capable of reacting with the compound of the Formula 1 to form a polymer. For example, any compound which is known to be useful for the formation of the phthalonitrile resin can also be used. Such curing agents are known in a variety of documents including the above-mentioned US patents.

In one example, an amine compound such as an aromatic amine compound or a hydroxy compound can be used as a curing agent. In the present application, the hydroxy compound may mean a compound containing at least one or two hydroxy groups in the molecule.

The present application also relates to a polymerizable composition. The polymerizable composition may comprise at least the above-described compound of Formula 1. The compound of Formula 1 can be self-cured without adding any additives, for example, a curing agent. Therefore, the polymerizable composition may further comprise a curing agent together with the compound of Formula 1, but such a curing agent is not necessarily required.

As the curing agent contained in the polymerizable composition, for example, a curing agent such as those already described can be used. As the curing agent known to be suitable for the formation of the phthalonitrile resin, an aromatic amine compound, a phenol compound, an inorganic acid, an organic acid, a metal or a metal salt, and the like can be exemplified, without being limited thereto.

The ratio of the curing agent in the polymerizable composition is not particularly limited. The ratio can be adjusted so that the desired curability can be ensured, for example, in consideration of the ratio or kind of the curable component such as the compound of the Formula 1 contained in the composition. For example, the curing agent may be included in an amount of about 0.02 to 1.5 moles per mole of the compound of Formula 1 contained in the polymerizable composition. However, the above ratios are only examples of the present application. Usually, if the ratio of the curing agent in the polymerizable composition is high, the process window tends to be narrowed, whereas if the ratio of the curing agent is low, the curability tends to become insufficient, so that the suitable ratio of the curing agent can be selected in consideration of this point.

The polymerizable composition of the present application can exhibit a low melting temperature and a wide process window while having excellent curability.

In one example, the polymerizable composition may have a processing temperature, i.e., a melting temperature or a glass transition temperature in a range of 100° C. to 300° C. In this case, the polymerizable composition may have a process window, that is, an absolute value of a difference (To−Tp) between the processing temperature (Tp) and the curing reaction initiation temperature (To) of the compound of Formula 1, of 50° C. or more, 70° C. or more, or 100° C. or more. In the present application, the term curing reaction initiation temperature may mean a temperature at the time when polymerization or curing of the polymerizable composition or a prepolymer to be described below is started. In one example, the curing reaction initiation temperature (To) may be higher than the processing temperature. Such a range may be advantageous for securing proper processability, for example, in the process of producing a composite to be described below by using a polymerizable composition. Here, the upper limit of the process window is not particularly limited, but for example, the absolute value of the difference (To–Tp) between the processing temperature (Tp) and the curing reaction starting temperature (To) may be 300° C. or less, or 200° C. or less.

The polymerizable composition may further comprise various additives, including other phthalonitrile compounds and the like, in addition to the compound of the Formula 1. As an example of such an additive, various fillers can be exemplified. The kind of the material that can be used as the filler is not particularly limited, and any known suitable filler may be used depending on the intended uses. The exemplary filler includes a metal material, a ceramic material, glass, a metal oxide, a metal nitride or a carbon-based material, and the like, but is not limited thereto. Furthermore, the type of the filler is not particularly limited as well and may be various forms, such as fibrous materials such as aramid fibers, glass fibers, carbon fibers or ceramic fibers, or woven fabrics, nonwoven fabrics, strings or cords, formed by the materials, particulates comprising nanoparticles, polygons or other amorphous forms. Here, as the carbon-based materials, graphite, graphene or carbon nanotubes, and the like, or derivatives or isomers such as oxides thereof, and the like can be exemplified.

The present application also relates to a prepolymer formed by reaction of the polymerizable composition, that is, the polymerizable composition comprising the compound of Formula 1.

In the present application, the term prepolymer state may mean a state where the compound of Formula 1 and the curing agent in the polymerizable composition are in a state polymerized in a certain degree (for example, a state that polymerization of a so-called stage A or B step occurs), without reaching a completely polymerized state, and exhibit an appropriate fluidity, for example, allow to process a composite to be described below.

The prepolymer may also exhibit excellent curability, a suitable processing temperature and a wide process window. In addition, the prepolymer may exhibit stability over time even when it is stored at room temperature for a long period of time.

In one example, the prepolymer may have a processing temperature, i.e., a melting temperature or a glass transition temperature in a range of 100° C. to 300° C. In this case, the prepolymer may have a process window, that is, an absolute value of a difference (To–Tp) between the processing temperature (Tp) and the curing reaction initiation temperature (To) of the prepolymer, of 50° C. or more, 70° C. or more, or 100° C. or more. In one example, the curing reaction initiation temperature (To) may be higher than the processing temperature. Such a range may be advantageous for securing proper processability, for example, in the process of producing a composite to be described below by using a prepolymer. Here, the upper limit of the process window is not particularly limited, but for example, the absolute value of the difference (To–Tp) between the processing temperature (Tp) and the curing reaction starting temperature (To) may be 300° C. or less, or 200° C. or less.

The prepolymer may further comprise any known additives in addition to the above components. As an example of such an additive, the above-described filler, and the like can be exemplified, without being limited thereto.

The present application also relates to a composite. The composite may comprise the above-described phthalonitrile resin and filler. As described above, it is possible to achieve excellent curability, a low melting temperature and a wide process window through the compound of the Formula 1 of the present application, and accordingly, a so-called reinforced resin composite (reinforced polymer composite) with excellent physical properties comprising various fillers can be easily formed. The composite thus formed may comprise the phthalonitrile resin and filler and may be applied to, for example, various applications, including durables such as automobiles, airplanes or ships, and the like.

The kind of the filler is not particularly limited and may be suitably selected in consideration of the intended use. As the usable filler, fibrous materials such as carbon fibers, aramid fibers, glass fibers or ceramic fibers, or woven fabrics, non-woven fabrics, strings or cords formed by the materials, or carbon nanomaterials such as carbon nanotubes or graphenes, and the like can be exemplified, without being limited thereto.

Also, the ratio of the filler is not particularly limited, and may be set in an appropriate range depending on the intended use.

The present application also relates to a precursor for producing the composite, wherein the precursor may comprise, for example, the polymerizable composition and the filler as described above, or the prepolymer and the filler as described above.

The composite can be prepared in a known manner using the precursor. For example, the composite can be formed by curing the precursor.

In one example, the precursor may be prepared by blending the polymerizable composition, which is prepared by compounding the compound of Formula 1 described above with a curing agent in a molten state, or the prepolymer, with the filler in a state molten by heating or the like. For example, the above-described composite can be prepared by molding the precursor thus produced into a desired shape and then curing it. The polymerizable composition or prepolymer has a low melting temperature and a wide process temperature together with excellent curability, so that molding and curing can be efficiently performed in the above process.

In the above processes, the method for forming the prepolymer or the like, the method for producing the composite by compounding such a prepolymer with the filler, and processing and curing it, and the like may be carried out according to known methods.

The present application may also relate to a precursor for a phthalocyanine dye, a precursor for a fluorescent brightener or a precursor for a photographic sensitizer, comprising the compound, or an acid anhydride derived from the compound. The method for forming the precursor or the method for producing the acid anhydride, using the compound, is not particularly limited and all known methods capable of producing the precursor or acid anhydride using phthalonitrile compounds can be applied.

Advantageous Effects

The present application can provide a phthalonitrile compound and a use thereof. The phthalonitrile compound has a novel structure, and can exhibit an excellent effect in uses known for the phtalonitrile compound to be applicable. As such a use of the phthalonitrile compound, a raw material or precursor for, so-called, a phthalonitrile resin, a phthalocyanine dye, a fluorescent whitening agent, a photographic sensitizer, an acid anhydride, or the like can be exemplified.

BEST MODE

Hereinafter, the phthalonitrile resins of the present application and the like will be specifically described by way of Examples and Comparative Examples, but the scope of the resins and the like is not limited to the following examples.

MODE FOR INVENTION

1. Nuclear Magnetic Resonance (NMR) Analysis

The NMR analysis was performed according to the manufacturer's manual using a 500 MHz NMR instrument from Agilent. A sample for NMR measurement was prepared by dissolving the compound in DMSO (dimethyl sulfoxide)-d6.

2. DSC (Differential Scanning Calorimetry) Analysis

The DSC analysis was performed in N2 flow atmosphere, while raising the temperature from 35° C. to 450° C. at a rate of temperature increase of 10° C./min using a Q20 system from TA instrument.

3. TGA (Thermogravimetric Analysis) Analysis

The TGA analysis was performed using a TGA e850 instrument from Mettler-Toledo. In the case of the compounds prepared in Preparation Examples, they were analyzed in N2 flow atmosphere, while raising the temperature from 25° C. to 800° C. at a rate of temperature increase of 10° C./min.

Preparation Example 1. Synthesis of Compound (PN1)

Figure 1:
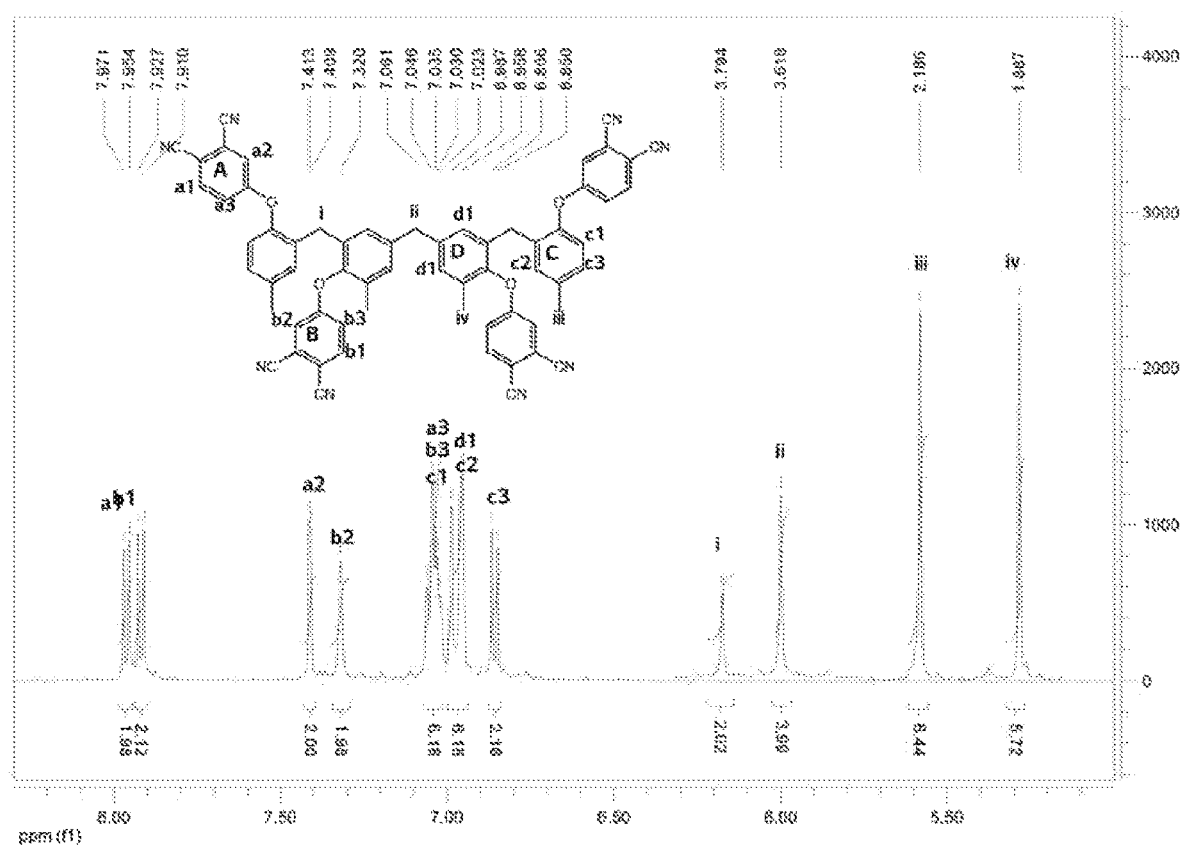
FIGS. 1 and 2 are NMR analysis results of the compounds prepared in Preparation Examples 1 and 2, respectively.

The compound of Formula A below was synthesized in the following manner. 103.09 g of 4,4'-methylenebis[2-[(2-hydroxy-5-methylphenyl)methyl]-6-methyl-phenol and 152.39 g of 4-nitrophthalonitrile were introduced into a three-necked reaction flask together with 145.95 g of potassium carbonate and 605.9 g of DMF (dimethyl formamide). As the reaction flask, a 1000 ml flask equipped with a mechanical stirrer, a distillation apparatus and a nitrogen inlet was used. Subsequently, a nitrogen stream was passed through the reaction flask, and the mixture was heated and stirred at a temperature of about 85° C. for about 5 hours. Subsequently, the mixture in the flask was cooled to room temperature (about 20° C. to 25° C.), and the mixture was precipitated in 4 L of an aqueous hydrochloric acid solution (concentration: 0.2N) and then filtered to remove residual inorganic salts and DMF. The powder obtained after filtration was dispersed again in methanol (1 L), filtered again to remove organic materials, and the reaction product was vacuum-dried in an oven at 50° C. to yield a target product. The results of NMR analysis carried out on the target product were attached to FIG. 1.

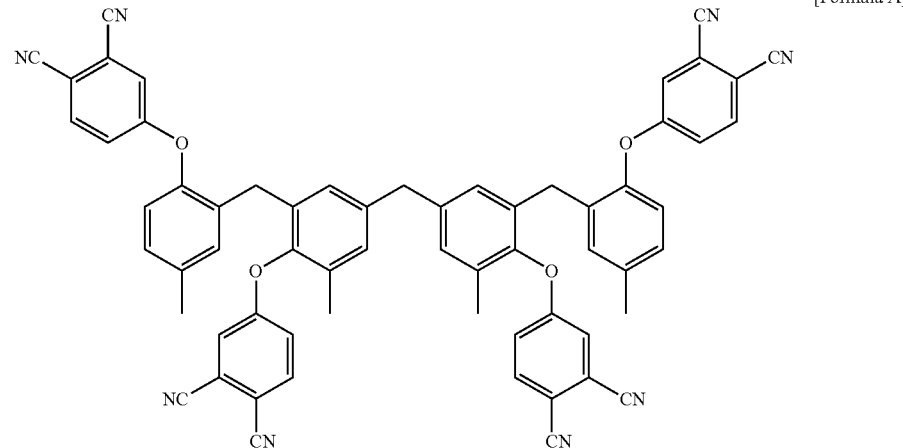

[Formula A]

Preparation Example 2. Synthesis of Compound (PN2)

Figure 2:
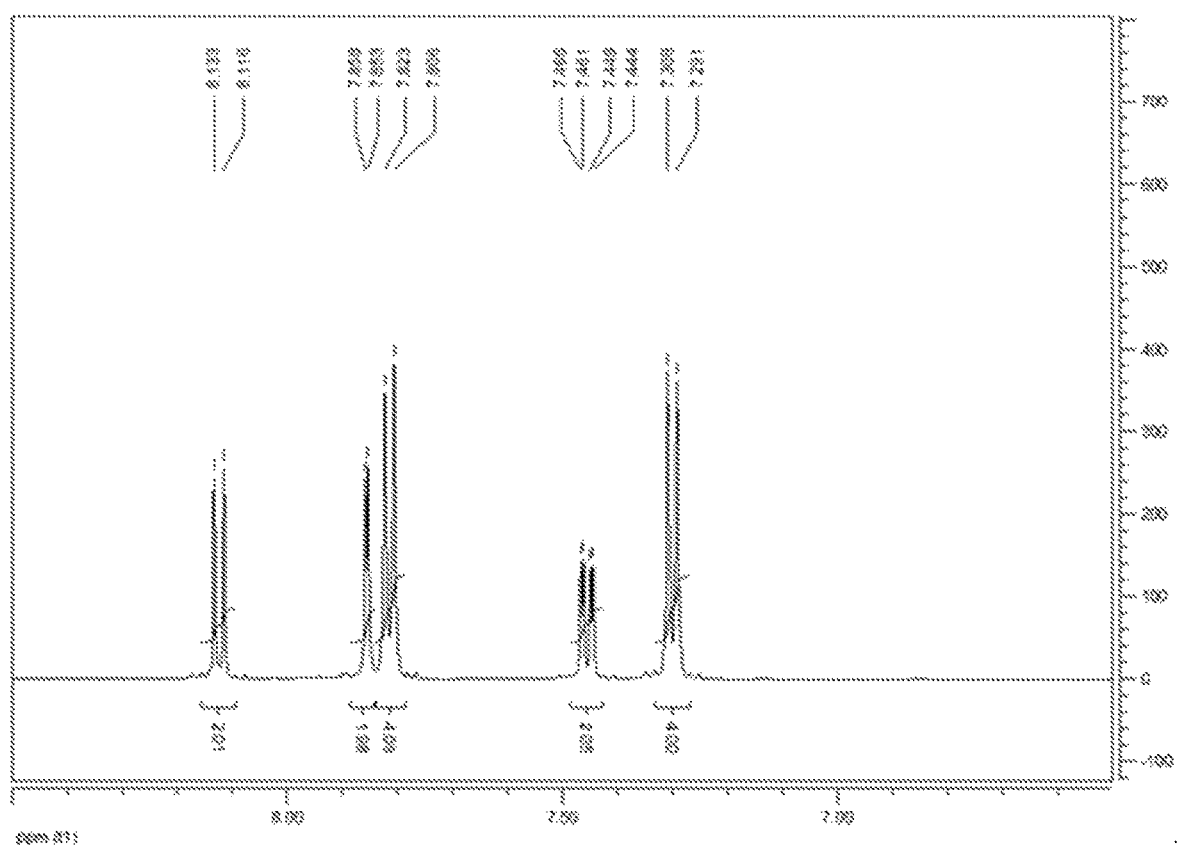

The compound of Formula B below was synthesized in the following manner. 27.9 g of 4,4'-biphenol and 100 mL of DMF (dimethyl formamide) were introduced into a 3 neck RBF (round bottom flask) and dissolved by stirring at room temperature. 51.9 g of 4-nitrophthalonitrile was added and 50 g of DMF was added, and then dissolved by stirring. Subsequently, 62.2 g of potassium carbonate and 50 g of DMF (dimethyl formamide) were introduced together, and then the temperature was raised to 85° C. while stirring. After reacting the mixture for about 5 hours, the reactant was cooled to room temperature (about 20° C. to 25° C.), and neutralized and precipitated in an aqueous hydrochloric acid solution (concentration: 0.2N). After filtering, it was washed with water. Then, the filtered reactant was vacuum-dried in an oven at 100° C., and after removal of water and residual solvent, the compound of Formula B below was obtained. The results of NMR analysis carried out on the target product were attached to FIG. 2.

[Formula B]

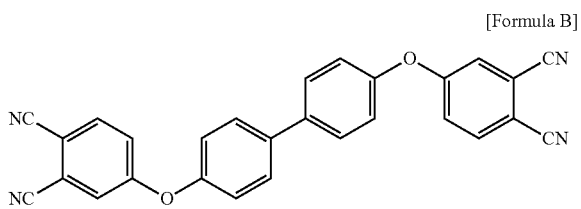 [SMILES: N#Cc1ccc(Oc2ccc(-c3ccc(Oc4ccc(C#N)c(C#N)c4)cc3)cc2)cc1C#N]

Example 1

To the compound of Formula A in Preparation Example 1, 18 mol % of a curing agent was added relative to the used amount of the compound of Formula A and mixed well to prepare a polymerizable composition. Here, as the curing agent, the compound of Formula C below was used, which is known to be usable in preparing the phthalonitrile resin. The results of DSC and TGA analyses carried out on the composition were shown in Table 1 below. A prepolymer can be prepared by heating the polymerizable composition at 240° C. for several minutes. The prepared prepolymer is heated for about 10 hours while again raising the temperature from 240° C. to about 375° C. to complete the thermosetting, whereby a phthalonitrile resin can be prepared.

[Formula C]

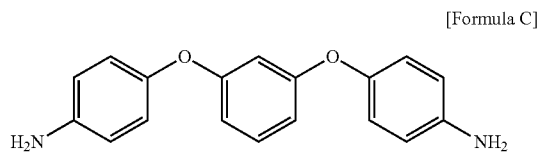 [SMILES: Nc1ccc(Oc2cccc(Oc3ccc(N)cc3)c2)cc1]

Example 2

A polymerizable composition was prepared using the compound of Formula A in Preparation Example 1 without further additives. The results of DSC and TGA analyses carried out on the composition were shown in Table 1 below. The prepolymer can be prepared by heating the polymerizable composition at 240° C. for several minutes. The prepared prepolymer is heated for about 10 hours while again raising the temperature from 240° C. to about 375° C. to complete the thermosetting, whereby a phthalonitrile resin can be prepared.

Comparative Example 1

A polymerizable composition was prepared in the same manner as in Example 1, except that the compound of Formula B in Preparation Example 2 was used instead of the compound of Formula A in Preparation Example 1. The results of DSC and TGA analyses carried out on the composition were shown in Table 1 below.

The results of DSC and TGA analyses carried out on the compositions of Examples and Comparative Examples are shown in Table 1 below.

TABLE 1

| | Processing temperature (° C.) | Exothermal onset temperature (° C.) | Press window (° C.) | Residue (%) at 800° C. |
|---|---|---|---|---|
| Example 1 | 107 | 277 | 170 | 78.4 |
| Example 2 | 110 | 338 | 228 | 79.1 |
| Comparative Example 1 | 233 | 261 | 28 | 78.92 |

From the results of Table 1, it can be confirmed that in the case of using the compound of the present invention the composition has a low processing temperature, so that it is possible to process the composition at low temperature or to prepare the prepolymer, the wide process window of 100° C. or more is secured and the composition exhibits excellent heat resistance. In addition, as confirmed from the case of Example 2, it can be confirmed that the self-curing of the compound of Formula 1 is possible, even when no curing agent is used.

The invention claimed is:

1. A phthalonitrile resin comprising polymerized units derived from a compound represented by Formula 1 below:

[Formula 1]

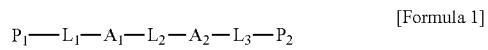

wherein, $P_1$ and $P_2$ are the same or different aryl groups from each other, $A_1$ and $A_2$ are the same or different arylene groups from each other, $L_1$ to $L_3$ are each independently an alkylene group, an alkylidene group, an alkenylene group or an alkynylene group, and $P_1$, $P_2$, $A_1$ and $A_2$ are each substituted with at least one substituent represented by Formula 2 below,

[Formula 2]

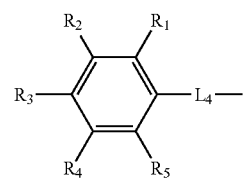

wherein, $L_4$ is an alkylene group, an alkylidene group, an oxygen atom or a sulfur atom, and $R_1$ to $R_5$ are each independently hydrogen, an alkyl group, an alkoxy group, an aryl group or a cyano group, provided that at least two of $R_1$ to $R_5$ are a cyano group.

2. The resin according to claim 1, wherein $L_1$ to $L_3$ are each independently an alkylene group or alkylidene group having 1 to 4 carbon atoms.

3. The resin according to claim 1, wherein $P_1$, $P_2$, $A_1$ and $A_2$ are each substituted with at least one alkyl group.

4. The resin according to claim 1, wherein $A_1$ and $A_2$ are a phenylene group.

5. The resin according to claim 4, wherein $L_1$ is bonded to the meta position based on the position combined with $L_2$ in $A_1$, and $L_3$ is bonded to the meta position based on the position combined with $L_2$ in $A_2$.

6. The resin according to claim 4, wherein the substituent of Formula 2 is substituted at the meta or para position based on to the position combined with $L_2$ in $A_1$, and the substituent of Formula 2 is substituted at the meta or para position based on the position combined with $L_2$ in $A_2$.

7. The resin according to claim 4, wherein the alkyl group having 1 to 4 carbon atoms is substituted at the meta or para position based on to the position combined with $L_2$ in $A_1$, and the alkyl group having 1 to 4 carbon atoms is substituted at the meta or para position based on the position combined with $L_2$ in $A_2$.

8. The resin according to claim 1, wherein $P_1$ and $P_2$ are a phenyl group.

9. The resin according to claim 8, wherein the substituent of Formula 2 is substituted at the otho or meta position based on the position combined with $L_1$ in $P_1$, and the substituent of Formula 2 is substituted at the otho or meta position based on the position combined with $L_3$ in $P_2$.

10. The resin according to claim 8, wherein the alkyl group having 1 to 4 carbon atoms is substituted at the otho or meta position based on the position combined with $L_1$ in $P_1$, and the alkyl group having 1 to 4 carbon atoms is substituted at the otho or meta position based on the position combined with $L_3$ in $P_2$.

11. A composite comprising the phthalonitrile resin of claim 1 and a filler.

* * * * *